United States Patent [19]

Coury et al.

[11] 4,226,244
[45] Oct. 7, 1980

[54] ELECTRICAL CONNECTOR FOR IMPLANTABLE ELECTRICAL GENERATORS

[75] Inventors: Arthur J. Coury, St. Paul; Frank J. Wilary, Plymouth, both of Minn.

[73] Assignee: Medtronic, Inc., Minneapolis, Minn.

[21] Appl. No.: 929,315

[22] Filed: Jul. 31, 1978

[51] Int. Cl.[3] ............................................. A61N 1/36
[52] U.S. Cl. ................................................. 128/419 P
[58] Field of Search ........ 128/419 P, 419 PG, 419 PS

[56] References Cited

U.S. PATENT DOCUMENTS

| | | | |
|---|---|---|---|
| 3,683,932 | 8/1972 | Cole | 128/419 P |
| 3,908,668 | 9/1975 | Bolduc | 128/419 P |
| 4,105,037 | 8/1978 | Richter et al. | 128/419 P |
| 4,142,532 | 3/1979 | Ware | 128/419 P |

*Primary Examiner*—William E. Kamm
*Attorney, Agent, or Firm*—Schroeder, Siegfried, Ryan, Vidas, Steffey & Arrett

[57] ABSTRACT

A preformed electrical connector for use with body implantable stimulators, such as heart pacemakers, having a signal generator and at least one electrical lead electrically and mechanically connected to each other through the preformed electrical connector. The connector carries at least one terminal to establish electrical contact between the signal generator and electric lead, passageways being provided in the connector body to accept and guide the signal generator feedthrough pin and electrical lead into contact with the terminal. In a preferred embodiment, the terminal is provided with intersecting bores such that the feedthrough pin and electrical lead form electrical contact within or by means of the terminal. The pin may be welded or press fit to the terminal and the lead may be attached to the terminal by means of a setscrew. The preformed connector may be mechanically fastened or fastened with an adhesive to the implantable stimulator. The connector may include one or two terminals and may then connect one or two sets of feedthrough pins and respective electrical lead wires.

1 Claim, 4 Drawing Figures

U.S. Patent     Oct. 7, 1980     4,226,244
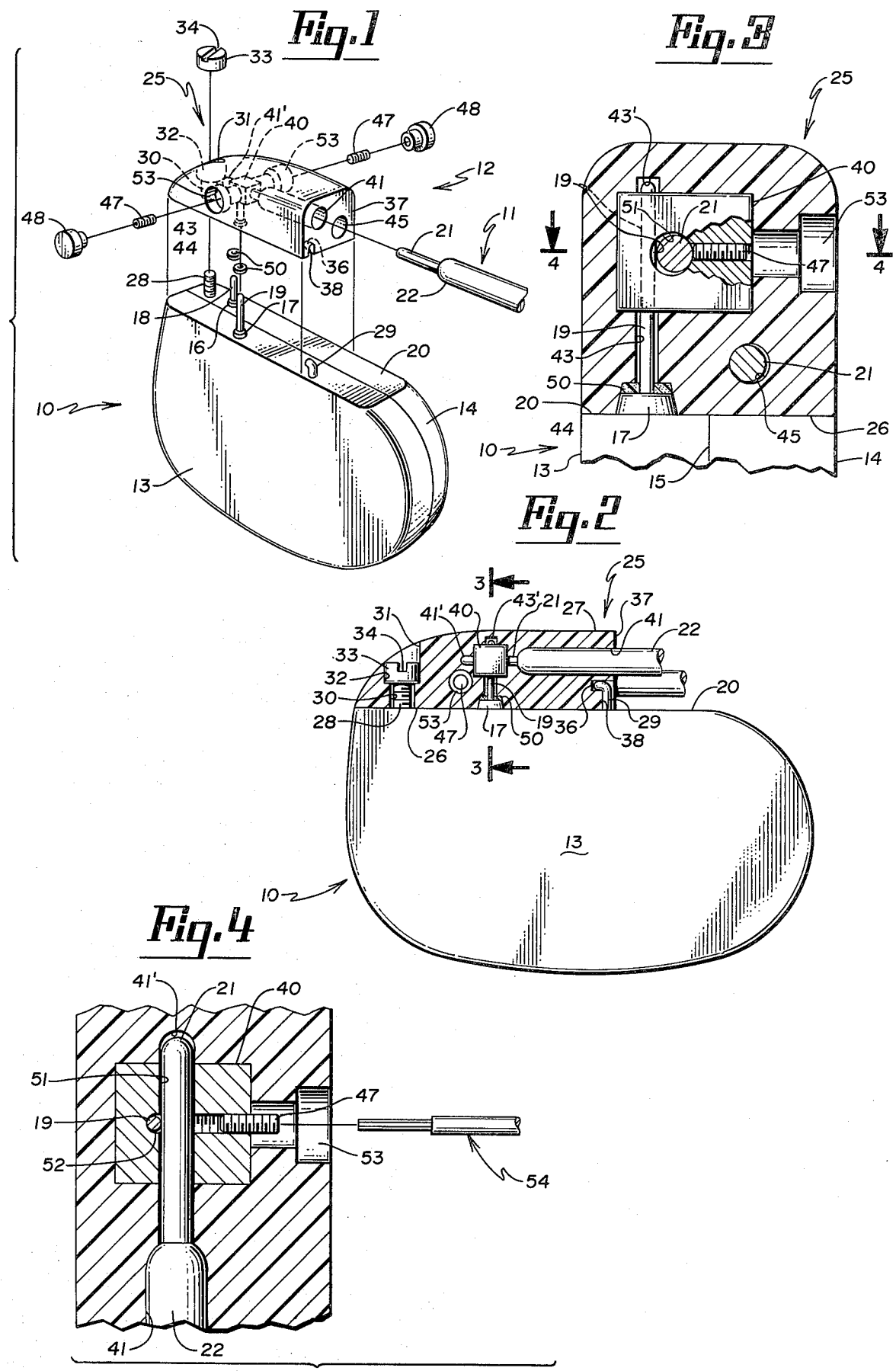

ELECTRICAL CONNECTOR FOR IMPLANTABLE ELECTRICAL GENERATORS

BACKGROUND OF THE INVENTION

Body implantable stimulators are known to the prior art, the most common being the cardiac or heart pacemaker. Typically, such stimulators are formed of a separable electrical lead and a signal generator with provision being made to electrically and mechanically connect the lead and generator to complete the stimulator unit.

Many prior art signal generators have been found following assembly by casting the components, including mechanical and electrical connections for the lead, in a matrix of encapsulating material which supports the components and shields them from the body environment. Typically, the encapsulating material is an epoxy.

In the body environment, it is generally recognized that an enclosed and hermetically sealed signal generator is more reliable as a result of the known and controlled environment provided by the hermetic seal. For this reason, many recent signal generator designs include a rigid enclosure formed of a plurality of preformed members which are typically welded together to complete the enclosure. The connection between the generator and the electrical lead, when it is desired that these members be separable, occurs outside of such an enclosure. It is common to cast an interconnect assembly from epoxy. However, it would be beneficial to eliminate the epoxy encapsulation process. Thus, a preformed connector assembly, which may be reliably secured to a preformed enclosure housing the generator components, would greatly facilitate assembly of the stimulator. The amount of handling would be reduced with the remaining handling being easier to perform than an epoxy casting process. One type of preformed connector assembly is disclosed in application Ser. No. 793,642, filed May 4, 1977, in the name of Richard A. Jones and now issued as U.S. Pat. No. 4,154,248, which application is commonly owned with the present application.

The above referenced application provides a preformed connector assembly thereby eliminating the necessity of forming that assembly in place, as by an epoxy casting process, for example. In that assembly, the electrical connection between the connector assembly terminal and the signal generator requires manipulation of a wire to position it and a weld, or other similar process, to secure it in position. Thus, while the connector assembly of the above referenced application greatly reduces the handling necessary to form and complete a connector assembly on a signal generator unit, considerable handling remains necessary.

SUMMARY OF THE INVENTION

The present invention provides a preformed connector with encapsulated terminal for attachment to the generator. It eliminates the use of epoxy or other similar substances to encapsulate the terminal after attachment of the terminal to the generator. This approach allows quality assurance of each preformed connector prior to assembly or attachment to the generator. The amount of handling necessary to assemble the stimulator and establish the proper electrical connections is reduced.

In a preferred embodiment, the preformed connector is provided with passageways which accept and guide the signal generator output connections (usually a feedthrough pin or pins) and the electrical lead into electrical contact with a terminal in the connector. One or more terminals are provided with intersecting bores such that the feedthrough pin and electrical lead contact within the terminal or by means of it. Means are provided for securing the lead within the terminal. For example, this may be accomplished via a set screw which engages the lead to urge it against the terminal. The feedthrough pin may be welded or otherwise secured to the terminal as by a press fit for example.

BRIEF DESCRIPTION OF THE DRAWINGS

FIG. 1 is an exploded view of an embodiment of the present invention.

FIG. 2 is a partial cutaway of the embodiment of FIG. 1, as assembled.

FIG. 3 is a cross section taken along the line 3—3 in FIG. 2.

FIG. 4 is a cross section taken along the line 4—4 in FIG. 3.

DETAILED DESCRIPTION OF THE DRAWINGS

Referring now to FIG. 1, there is illustrated an exploded view of a preferred embodiment of the electrical connector of the present invention. FIG. 1 also shows generally an implantable signal generator 10, electrical lead 11, and the preformed connector 12 of the invention which, when assembled with the other parts, constitutes a heart pacemaker. Signal generator 10 includes all the necessary signal generating components and power sources within an enclosure formed of two body members 13 and 14 joined together at a seam 15 in known manner, as by welding, for example. Electrical feedthroughs 16 and 17 provide electrical communication with the enclosed signal generating component, in known manner, the feedthroughs having electrical connections or feedthrough pins 18 and 19. Feedthroughs 16 and 17 extend from a surface 20 which is adapted to receive preformed connector 12 in a manner to be described more fully below. Electrical lead 11 is of the type having a pin connection 21 and insulating body 22 which surrounds and protects an electrical conductor (not shown). In use lead 11 extends from generator 10 to contact the heart muscle of the user to deliver pulses to the heart.

Connector 12 includes a body portion 25 which may be formed in any known manner, as by molding, for example. Preferably, body 25 is of a clear material so as to allow visual verification of the electrical connections. Body 25 may be formed of many known materials including, polysulfone as sold under the tradename UDEL by Union Carbide, polyurethane as sold under the tradename PELLETHANE by Upjohn, polymethylpentene as sold under the tradename TPX by Mitsui and Company, polyvinylidene fluoride as sold under the tradename KYNAR, and ethylenechlorotrifluoroethylene as sold under the tradename HALAR by the Allied Chemical Corporation.

The undersurface 26 of body 25 is adapted to rest on surface 20 of signal generator 10 while the outer surface 27 is configured so as to extend the general outer configuration of signal generator 10 when surfaces 20 and 26 are mated. Many types of mechanical connections or adhesives may be used for this purpose. A typical mechanical arrangement is described herein for illustration although many arrangements will be formed to be satisfactory.

Extending from surface 20 is a threaded stud 28 and hook member 29. An aperture 30 extends from the under surface 26 of body 25 and joins a second aperture 31 extending from surface 27. Aperture 30 is large enough to accommodate threaded stud 28 while aperture 31 is large enough to accommodate a threaded nut 33. The junction of the apertures 30 and 31 forms a shoulder 32 on which nut 33 rests. Nut 33 is provided with a slot 34 so that it may be tightened on threaded stud 28 in the known manner. Of course, other tools may be employed requiring a different configuration in the recess shown as slot 34. For example, a hexagonal recess may be employed in conjunction with a tool of hexagonal cross section.

A second aperture 36 extends into body 25 from its face 37. Aperture 36 is adapted to accept the hook portion of hook 29 while the recess 38 on the face 37 is adapted to accept the lower portion of hook 29. On assembly, hook portion of hook 29 is inserted into recess 36 to engage it side wall and threaded stud 28 is inserted into aperture 30. Nut 33 then engages the threads on stud 28 and is tightened against the shoulder 32 to secure body 25 to the platform 20 and signal generator 10. This assembly is illustrated in FIG. 2.

Contained within body 25 are conductive terminals 40, one terminal for each lead 11. The illustrated embodiment is intended for bi-polar stimulation. However, for the purposes of clarity, only one lead 11 and one terminal 40 are shown in FIG. 1. A portion of a second lead 11 can be seen in FIG. 2. An aperture 41 extends from face 37 of body 25 to terminal 40 with an extension 41' extending from terminal 40. Aperture 41 accepts lead 11 and guides pin 21 into electrical contact with terminal 40. Similarly, an aperture 43 extends from the undersurface 26 of body 25 to terminal 40 for the purpose of accepting and guiding feedthrough pin 19 into electrical contact with terminal 40. Aperture 43 includes an enlarged portion 44 which accommodates feedthrough 17. Similar apertures and terminals are provided for feedthrough 16 and feedthrough pin 18. For example, an aperture 45 extends from face 37 to a terminal to accommodate a second lead. Aperture 53 in surface 27 allow access to set screws 47 carried by terminals 40 to lock pin 21 of lead 11 in position. Grommets 48 may be employed to seal the set screw apertures 53 while allowing access to the set screws, in know manner. Resilient washers 50 are provided which include a central aperture which accepts feedthrough pins 18 and 19 to rest atop feedthroughs 16 and 17. When the undersurface 26 of body 25 and surface 20 of generator 10 are mated, the shoulder formed between apertures 43 and 44 compresses the washers 50 against the top of feedthroughs 16 and 17 to seal pins 18 and 19 from the body environment.

Referring now to FIG. 3, there is illustrated a cross section of body 25 taken along lines 3—3 in FIG. 2. As illustrated in FIG. 3, terminal 40 includes a bore 51 which is adapted to accept pin 21 of lead 11. The aperture 41 of body 25 accepts lead 11 and guides pin 21 to and through bore 51. If body 25 is made of a transparent material, as preferred, the extension of pin 21 through bore 51 and into aperture 41' provides visual assurance of proper placement of pin 21 relative to terminal 40. A second bore 52 in terminal 40 (see FIG. 4) receives pin 19 of feedthrough 17, aperture 43 accepting pin 19 and guiding it to bore 52. An extension 43' of aperture 43 may be provided to allow visual verification of proper positioning of pin 19 relative to the terminal 40. In the illustration of FIG. 3, lead 11 is not positioned within aperture 41 or bore 51 so as to illustrate the intersection of the bores 51 and 52 within terminal 40, pin 19 being visible through bore 51. As described above, an aperture 53 is provided for access to set screw 47. Set screw may be provided on its end with a hexagonal recess for cooperation with a tool 54 (see FIG. 4) having a similar cross section at its terminus, in known manner.

FIG. 4 is a cross section taken along line 4-4 in FIG. 3 and further illustrates the intersection of bores 51 and 52, the intersection preferably being in line with the set screw. That is, as set screw 47 is tightened against pin 21, pin 21 is urged against feedthrough 19 thereby securing both pin 21 and connection 19 in place within terminal 40. This further assures an electrical communication between connection 19 and pin 21. However, other configurations may be employed so long as the pin 21 and connection 19 are in contact with each other or with conductive terminal 40.

Obviously, many modifications and variations of the present invention are possible in light of the above teachings. As pointed out above, other securement systems may also be employed consistent with the present invention. For examples thereof, reference is made to application Ser. No. 894,358, filed Apr. 7, 1978, and application Ser. No. 894,359, filed Apr. 7, 1978, both of which are commonly owned with the present application. Also, aperture 43 need not guide pin 19 through a bore in terminal 40, but, instead, need only guide it into contact with that terminal 40. If pin 19 is guided to a location adjacent to terminal 40, and the material for which the body 25 is made sufficiently transparent, pin 19 and terminal 40 may be welded to each other through the body material by known techniques. Further, pin 19 may be welded within the bore 52 of FIG. 4 through the aperture engaged by the set screw 47 with the set screw 47 removed. Modification to accommodate unipolar stimulation is within the skill of one ordinarily skilled in the art. Accordingly, within the scope of the appended claims, the invention may be practiced other than as specifically described.

What I claimed is:

1. An electrical connector for attachment to an implantable electrical generator and for connecting an electrical feedthrough lead of the generator to a lead wire, of which there may be one or more of each, comprising: preformed body means formed of a molded biocompatible plastic material and having one surface thereof adapted to rest on the signal generator for connection thereto, terminal means in said body adapted to receive and connect the feedthrough lead and the lead wire, the terminal means having first and second bore means and the preformed connector means comprising first and second corresponding aperture means respectively associated with the first and second bore means, the first and second aperture means accepting and guiding the feedthrough lead and lead wire respectively into the first and second bore means, and the first bore means extending to the connector surface adapted for contact with the electrical generator.